United States Patent [19]

Müller et al.

[11] Patent Number: 4,968,483

[45] Date of Patent: Nov. 6, 1990

[54] APPARATUS FOR THE PRODUCTION OF OXYGENATED BLOOD

[75] Inventors: Alexander Müller, Essen; Hans-Dieter Jentiens, Radevormwald-Bergerhof, both of Fed. Rep. of Germany

[73] Assignee: Quarzlampenfabrik Dr.-Ing. Felix W. Muller GmbH & Co. KG, Essen, Fed. Rep. of Germany

[21] Appl. No.: 117,519

[22] Filed: Nov. 4, 1987

[30] Foreign Application Priority Data

Jan. 15, 1987 [DE] Fed. Rep. of Germany ... 8700628[U]
Mar. 26, 1987 [DE] Fed. Rep. of Germany ... 8704467[U]

[51] Int. Cl.$^5$ .............................................. A61M 1/14
[52] U.S. Cl. ........................................ 422/45; 422/24; 250/495.1; 250/504 R
[58] Field of Search ................. 422/45, 24; 250/495.1, 250/496.1, 504 R

[56] References Cited

U.S. PATENT DOCUMENTS 2,827,901 3/1958 Jones ...................................... 422/45

FOREIGN PATENT DOCUMENTS 2456932 6/1976 Fed. Rep. of Germany ........ 422/45

Primary Examiner—Robert J. Warden
Assistant Examiner—Lynn Kummert
Attorney, Agent, or Firm—Herbert Dubno

[57] ABSTRACT

An apparatus is disclosed for the production of oxygenated blood. The apparatus incorporates a vessel for containing the blood that is to be processed, an ultraviolet lamp and an infrared lamp being associated with the vessel. A feed pipe extends into the vessel to a position near the bottom of the vessel, such feed pipe being connected to a source of ozone. The vessel is essentially in the form of an inverted bottle, the neck opening of which is closed and the base of which incorporates a central opening for the feed pipe, the vessel and the feed pipe being designed as disposable items. The vessel is installed in the area of a working surface of the apparatus so as to be releasable therefrom, while the feed pipe is connectable to a coupling on a line that leads to the ozone source.

31 Claims, 2 Drawing Sheets

APPARATUS FOR THE PRODUCTION OF OXYGENATED BLOOD

FIELD OF THE INVENTION

The present invention relates to an apparatus for the production of oxygenated blood, said apparatus incorporating a vessel to contain the blood that is to be treated, an ultraviolet lamp and an infrared lamp being associated with the container, a feed pipe that is connected to a source for ozone and that reaches to its bottom area extending into the container.

THE RELATED ART

It is known that for purposes of haematological oxidation therapy, after a stabilizing agent against coagulation has been added to it, human or animal blood can be processed with air while being irradiated with ultraviolet radiation; when this is done, the flow of air that is introduced into it converts the blood into foam that moves within the ultraviolet radiation. The foam that is so formed is destroyed by the blood returning to its liquid state. Oxygenated blood that is processed in this way can be injected intramuscularly or intravenously.

However, under certain conditions that have not been researched further, blood that has been oxygenated in this manner can give rise to shock reactions, a fact that renders haematological oxidation therapy difficult. The difficulties may be connected with the decomposition of erythrocytes when oxygen acts on the foamed blood, which can be recognized by the unpleasant smell of the reaction media.

In order to avoid these disadvantages, DE-PS 1 068 428 has proposed that ozone be passed through a continuous column of liquid, stabilized, venous blood in an area of ultraviolet radiation such that no significant foaming takes place, with the temperature being increased gradually to approximately 45° C. during this process. An approximately funnel-shaped vessel of material that is transparent to ultraviolet radiation is used, and this vessel is surrounded by a coiled ultraviolet quartz lamp as well as by an infrared radiator. A feed pipe enters the top of the processing vessel and extends within the vessel to a point close to its bottom; outside the processing vessel, this feed pipe is connected to an ozonizing chamber within which there is a low-pressure quartz lamp that ozonizes the oxygen that is supplied to the ozonizing chamber. This known apparatus has been found satisfactory, although it is comparatively costly to produce and extemely inconvenient to use.

Proceeding from this prior art, it is the object of the present invention to create an apparatus of the type described in the introduction hereto, which avoids the disadvantages set out above and which is not only simple to produce and install, but which, in addition, permits rapid and safe operation.

SUMMARY OF THE INVENTION

According to the present invention, this has been achieved in that the vessel is essentially in the form of an inverted bottle, the neck opening of which is closed, and the bottom of which incorporates a central opening for the feed pipe; both the vessel and the feed pipe are designed as disposable items. The vessel is installed in the area of a working surface of the apparatus so as to be releasable. The feed pipe can be connected to a coupling for a line that leads to the ozone source. This configuration results in rapid and safe operation, for the sterile vessel is filled with blood that is removed from the patient and is installed in a holder provided for this purpose as part of the apparatus, whereupon the sterile feed pipe in the form of a tube is inserted into one end until it is close to the bottom of the apparatus; the other end is connected to the coupling on the line that leads to the ozonizer. When the apparatus is switched on, the blood within the container is exposed to ultraviolet irradiation and to infrared heating to a maximum of 45° C., whereupon the apparatus is switched off and the oxygenated blood removed by means of a syringe and injected either intravenously or intramuscularly into the patient. The holders are released and the vessel and the feed pipe are removed from the apparatus and discarded so that further processing can take place with new sterile vessels and feed pipes.

The neck opening of the bottle is closed tightly by means of a cover that is curved outwards, so that a gap is left between the face end of the feed pipe that rests on the cover, the ozone that is introduced into the vessel being able to emerge unhindered through this gap.

The neck of the vessel, which is fitted with the cap, is of the approximate form of a lobe, so that the blood is retained in a comparatively small space to undergo intensive exposure to the ozone. The volume of the vessel is such that its contents are sufficient for a maximum quantity of foamed blood, with a specific reserve so that the foamed blood can never emerge from the opening of the vessel. The vessel is of low-density polyethylene that is of high quality, transparent to ultraviolet wavelengths, pyrogen-free, and can be sterilized by irradiation. These vessels are packed individually and sealed in pouches, whereby irradiation sterilization also renders them aseptic.

The vessel is surrounded by a plurality of low-pressure ultraviolet lamps that generate the ultraviolet radiation required for processing the blood in connection with haematological oxidation therapy. These low-pressure ultraviolet lamps generate a line spectrum in which it is preferred that the line 253.7 nm accounts for the greatest part of the radiation, namely, approximately 90 per cent. This results in highly-effective sterilization and a high degree of asepsis. The low-pressure ultraviolet lamps are U-shaped, it being preferred that four be provided, these being displaced at 90° relative to each other around the vessel. The low-pressure ultraviolet lamps can be produced and installed very simply because of their U-shape, so that only a comparatively small expenditure is needed to achieve this. It is preferred that the low-pressure ultraviolet lamps be produced from ozone-free quartz.

According to another feature of the present invention, the vessel and the greater part of the low-pressure ultraviolet lamps that surround it are enclosed by a U-shaped reflector so that the radiation emitted from the back and sides of the lamps is captured and reflected back onto the vessel, the walls of which are transparent to ultraviolet radiation, this ensuring a high degree of effectiveness of the ultraviolet radiation on the blood to be processed.

It is advantageous that the infrared lamp be arranged beneath the vessel, so that warming takes place from below. Such an arrangement permits an extremely compact structure which, at the same time, ensures intensive warming of the blood that is to be processed within the vessel.

The vessel is fitted with a thermometer so that the increase in temperature can be monitored and controlled very accurately. Like the feed pipe for the ozone, the thermometer can extend into the vessel. However, it is also possible to arrange the thermometer outside the vessel, for example, as a non-contact type thermometer. This latter arrangement entails the advantage that the thermometer need not be configured as a disposable item that has to be discarded, with the vessel and the feed pipe, once processing has been completed, but can be installed permanently as a result of the fact that it is installed outside the vessel.

It is advantageous that a thermocouple be used as the thermometer. On reaching a temperature of 42.5° C. this thermocouple transmits a pulse that switches the apparatus off. The thermocouple consists of a thick-wall glass tube within which two unlike metal wires, preferably of iron and of constantan, are arranged. The ends of these wires are connected to each other within the tip of the tube. The connection point of these two wires of the thermometer is imbedded in casting resin so as to ensure the optimum thermal transfer from the surrounding medium.

An ozonizer that is connected through a solenoid valve to an oxygen cylinder or the like serves as the source of ozone. The ozonizer is fitted with one or a plurality of low-pressure ultraviolet lamps and the radiation from these converts the oxygen from the oxygen cylinder into ozone. The low-pressure ultraviolet lamp(s) emit(s) a line spectrum in which line 183 nm accounts for the major part of the overall radiation, and this results in highly efficient generation of ozone. The ozonizer is connected to a normal power supply and is not powered by high-tension voltage, which ensures a longer service life. It is advantageous that the oxygen cylinder be fitted with a pressure monitoring system that indicates the charge pressure of the oxygen cylinder and which switches the apparatus off in the event that the pressure drops below a prescribed value.

It is also possible to use an oxygen-generating system in place of the oxygen cylinder, so that there is then no need to replace the oxygen cylinders.

According to a further feature of the present invention, the electrical circuit incorporates a master switch, a processing switch, and switches that control the low-pressure ultraviolet lamps, the infrared heater, and the ozonizer; all of the foregoing switches can be operated separately. The individual systems within the apparatus are advantageously interconnected so that when the processing switch is turned on, all the systems are activated; this ensures that when blood is being processed, this blood is not only supplied with ozone, but is also exposed to infrared and ultraviolet radiation. It is possible to switch the apparatus off by a timer switch or as a function of the blood temperature that is reached.

In addition to the foregoing, a timer and/or a counter can also be connected to the processing switch, in order to count the number of processing cycles completed, or the duration of the processing cycles.

It is advantageous that the feed tube consist of a thick-walled glass tube that can be connected to the source of the ozone by means of a short section of tubing, this resulting in a version that is durable and easy to use.

BRIEF DESCRIPTION OF THE DRAWING

An embodiment of the present invention is described in greater detail below, on the basis of the drawings appended hereto. These drawings show the following.

DETAILED DESCRIPTION

Figure 1:
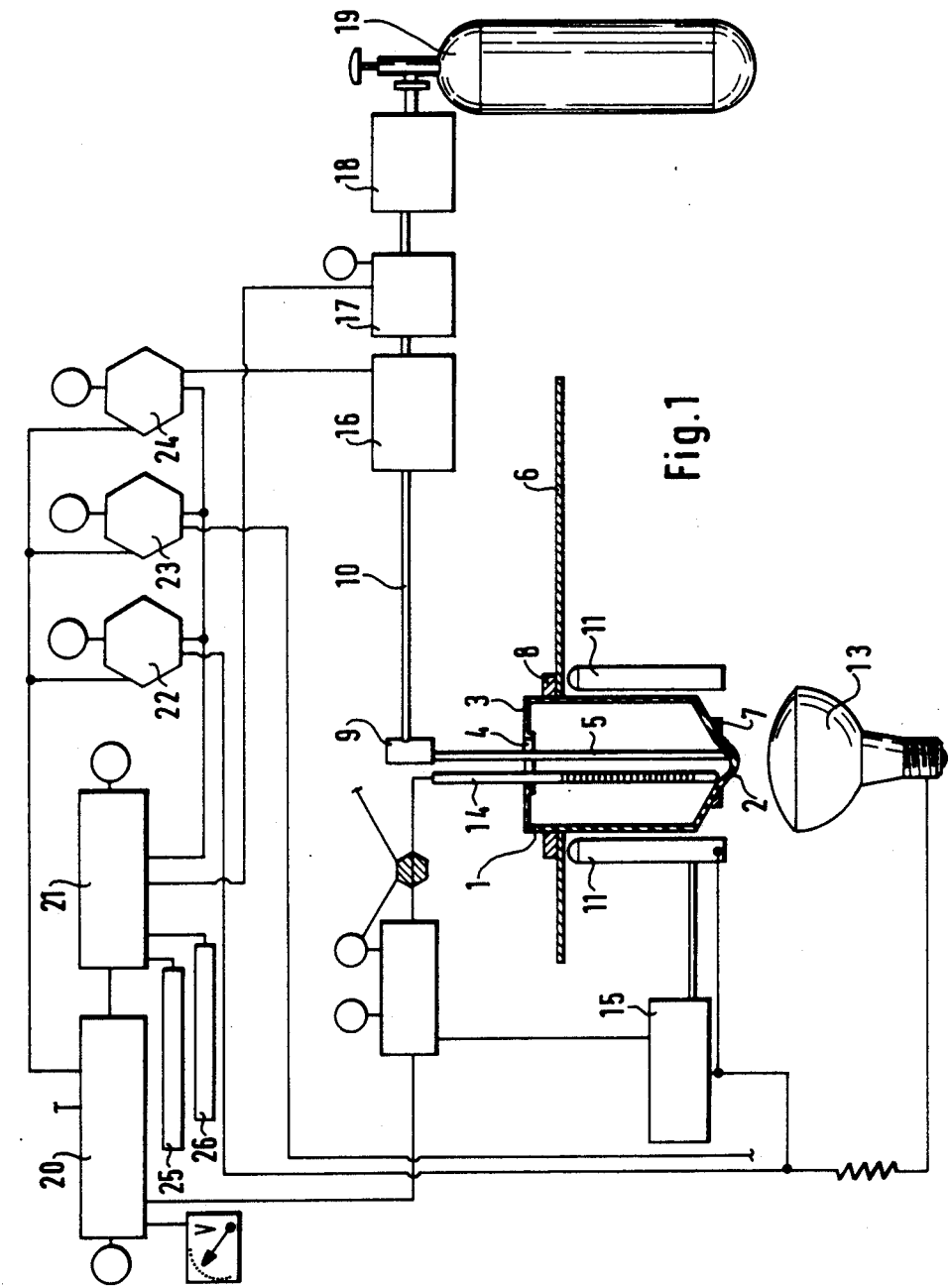
FIG. 1: A schematic representation of the circuit for the systems in the apparatus.

A vessel 1, essentially in the form of an inverted bottle, has its neck opening closed tightly by means of a cover 2. The vessel 1 is produced from low-density plastic, such as polyethylene, in the same manner as a milk jug. The base 3 of the vessel is provided with a central opening 4 for the feed pipe 5. The feed pipe 5, which is produced from plastic tubing, and the vessel 1 are produced as disposable items, so that these are discarded once they have been used.

The vessel 1 is installed so as to be removable in a working surface 6 in a holder, the holder not being shown in greater detail herein in the interests of clarity. To this end, the vessel is installed in a lower retaining ring 7 and in an upper retaining ring 8. Such an arrangement makes it possible to install the vessel in the apparatus quickly and easily, and then remove it from this once the blood has been processed.

The feed pipe 5 that extends into the vessel 1 can be connected at the coupling 9 on a line 10 that leads to an ozone supply system. This coupling 9 is a conventional pipe or tube coupling so that the feed pipe 5 can also be replaced quickly and easily.

The face surface of the lower end of the feed pipe 5 rests on the cover 2 of the vessel 1, this cover being curved outwards so that the ozone that is introduced can disperse through the gap formed in this way within the vessel 1 and then flow through the blood contained therein.

The vessel 1 is surrounded by a plurality of low-pressure ultraviolet lamps, these being of a U-shaped configuration in the embodiment shown. Four such lamps 11 are installed, and these are arranged at 90° to each other. The ultraviolet lamps 11 radiate a line spectrum in which line 253.7 nm accounts for the greater part of the radiation, for example, some 90 per cent, so that highly effective irradiation of the blood contained within the vessel 1 can be achieved, and together with this, the desired disinfection and sterilisation of the blood.

Figure 2:
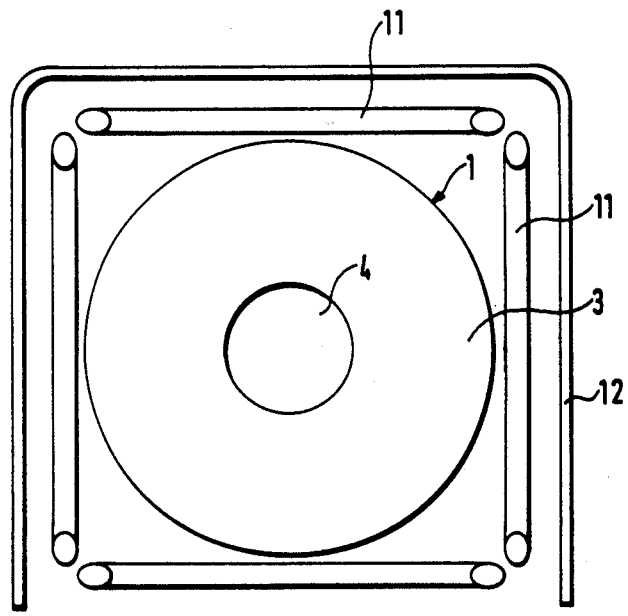
FIG. 2: A plan view of the vessel used to process the blood.

As can be seen from FIG. 2, the vessel 1 and the greater part of the low-pressure ultraviolet lamps 11 that surround the vessel, namely three of the burners, are surrounded by a U-shaped reflector 12, so that the radiation emanating from the low-pressure ultraviolet lamps 11 to the side and to the rear can also be utilized. Only one of the lamps 11 is not so enclosed, so that it is possible to monitor the vessel visually as the blood contained therein is being processed.

An infrared lamp 13 is arranged within the apparatus beneath the vessel 1; the output of this infrared lamp can be adjusted. The infrared radiation from this lamp warms the blood contained in the vessel 1, and the ozone passing through the blood simultaneously ensures that it is warmed uniformly.

In order that the extent to which the blood within the vessel can be monitored and adjusted, a thermometer extends into the vessel 1 through the opening 7 together with the feed pipe 5. In the embodiment shown, the thermometer 14 is also a disposable item so that this, together with the vessel 1 and the feed pipe 5, is replaced once the blood has been processed. However, it is also possible to provide a non-contact type thermometer, as a fixed component, in addition to or in place of the thermometer 14.

In the embodiment shown, an ozonizer 16 is used as a source of ozone; this ozonizer is connected to the line 10, and is connected through this and the solenoid valve 17 to an oxygen cylinder 19 that is fitted with a pressure gauge 18. The ozonizer 16 is fitted with at least one low-pressure ultraviolet lamp that also emits a line spectrum, line 183 nm accounting for the greatest part of the total radiation emitted by this lamp.

The electrical circuit for the apparatus incorporates a master switch 20, a processing switch 21, and switches 22, 23, and 24 for the infrared lamp 13, the ultraViolet lamps 11, and the ozonizer 16 respectively. The individual systems, discussed above, that make up the apparatus are so interconnected that all of them are activated when the processing switch 21 is set to the "On" position, thereby ensuring that the blood contained within the vessel 1 does in fact undergo processing by all the necessary components.

A timer 25 and/or a counter 26 can be connected to the processing switch 21.

All the components in the electrical circuit are safeguarded by warning lights so that it is always possible to monitor the proper operation of said components.

What is claimed is:

1. An apparatus for production of oxygenated blood, said apparatus comprising a vessel for containing blood that is to be processed, an ultraviolet lamp and an infrared lamp positioned to radiate output toward the vessel, a feed pipe extending into the vessel to a position near a bottom of the vessel, the feed pipe being connected to a source of ozone, wherein the vessel with a narrow neck and broad base at opposite ends is essentially in a form of an inverted bottle, a neck opening of which is closed and forms the bottom of the vessel, the base forming a top of the vessel and including means defining a central opening for the feed pipe, the vessel and the feed pipe being designed as disposable items, the vessel being installed in an area of a working surface of the apparatus so as to be releasable therefrom, while the feed pipe is connectable to a coupling on a line that leads to the ozone source.

2. An apparatus as defined in claim 1, wherein the neck opening of the bottle is firmly closed by a cover that is curved outwards.

3. An apparatus as defined in claim 2, wherein the neck of the vessel that is provided with a cover is in the approximate form of a lobe.

4. An apparatus as defined in claim 1, wherein the vessel is made of a material comprising a low-density polyethylene.

5. An apparatus as defined in claim 4, wherein the material for the vessel is of a high-quality, is transparent to ultraviolet wavelengths, is free of pyrogens, and can be sterilized by irradiation.

6. An apparatus as defined in claim 1, wherein the vessel is surrounded by a plurality of low-pressure ultraviolet lamps.

7. An apparatus as defined in claim 6, wherein the low-pressure ultraviolet lamps are produced from ozone-free quartz.

8. An apparatus as defined in claim 6, wherein the low-pressure ultraviolet lamps radiate a line spectrum in which line 253.7 nm accounts for the greatest part of the overall radiation.

9. An apparatus as defined in claim 8, wherein the low-pressure ultraviolet lamps radiate a line spectrum in which line 253.7 nm accounts for at least approximately 90 per cent of the overall radiation.

10. An apparatus as defined in claim 6, wherein the low-pressure ultraviolet lamps are U-shaped.

11. An apparatus as defined in claim 6, wherein four low-pressure ultraviolet lamps are positioned around the vessel.

12. An apparatus as defined in claim 6, wherein the vessel and a major part of the low-pressure ultraviolet lamps are surrounded by a U-shaped reflector.

13. An apparatus as defined in claim 1, wherein the infrared lamp is arranged beneath the vessel.

14. An apparatus as defined in claim 1, wherein a thermometer is in contact with the vessel.

15. An apparatus as defined in claim 14, wherein the thermometer extends into the vessel through the base of the vessel.

16. An apparatus as defined in claim 15, wherein the thermometer comprises a thermocouple.

17. An apparatus as defined in claim 16, wherein a means is provided permitting the thermocouple to transmit a pulse to switch off the apparatus when a temperature of 42.5° C. is reached.

18. An apparatus as defined in claim 16, wherein the thermocouple consists of a thick-walled glass tube, within which two wires of dissimilar metal are arranged, the ends of which are connected to each other in a tip of the glass tube.

19. An apparatus as defined in claim 18, wherein the point of connection of the two wires forming the thermocouple is imbedded in casting plastic.

20. An apparatus as defined in claim 18, wherein the thermocouple wires of dissimilar metal are iron and constantan.

21. An apparatus as defined in claim 14, wherein the thermometer is arranged outside the vessel.

22. An apparatus as defined in claim 21, wherein a non-contact type of thermometer is used as the thermometer.

23. An apparatus as defined in claim 1, wherein the feed pipe consists of a thick-walled glass tube connected to the source of ozone by means of a short section of tubing.

24. An apparatus as defined in claim 1, wherein an ozonizer is used as a source of ozone, connected to an oxygen cylinder through a solenoid valve.

25. An apparatus as defined in claim 24, wherein the ozonizer has at least one low-pressure ultraviolet lamp that radiates a line spectrum in which line 183 nm accounts for the greatest part of the total radiation.

26. An apparatus as defined in claim 24, wherein the ozonizer is connected to means providing a normal voltage.

27. An apparatus as defined in claim 24, wherein the oxygen cylinder is fitted with a pressure-monitoring system.

28. An apparatus as defined in claim 24, wherein an oxygen generator is used in place of an oxygen cylinder.

29. An apparatus as defined in claim 24, further including an electrical circuit which comprises a master switch, a processing switch, and switches for the infrared lamp, the ultraviolet lamps and the ozonizer, and wherein each of the switches can be operated independently.

30. An apparatus as defined in claim 29, wherein all the switches are so connected to each other that all the switches are activated when the processing switch is turned on.

31. An apparatus as defined in claim 29, wherein a timer and/or a counter is/are connected to the processing switch.

* * * * *